(12) United States Patent
Holland

(10) Patent No.: US 9,386,913 B2
(45) Date of Patent: Jul. 12, 2016

(54) TONGUE DEPRESSOR

(75) Inventor: Jennifer Louise Holland, Redhead (AU)

(73) Assignee: Throat Scope Pty Ltd, Redhead, New South Wales (AU)

(*) Notice: Subject to any disclaimer, the term of this patent is extended or adjusted under 35 U.S.C. 154(b) by 117 days.

(21) Appl. No.: 13/817,071

(22) PCT Filed: Aug. 18, 2011

(86) PCT No.: PCT/AU2011/001061
§ 371 (c)(1),
(2), (4) Date: Feb. 14, 2013

(87) PCT Pub. No.: WO2012/021937
PCT Pub. Date: Feb. 23, 2012

(65) Prior Publication Data
US 2013/0158358 A1    Jun. 20, 2013

Related U.S. Application Data

(60) Provisional application No. 61/374,947, filed on Aug. 18, 2010, provisional application No. 61/409,438, filed on Nov. 2, 2010.

(51) Int. Cl.
*A61B 13/00* (2006.01)
*A61B 1/24* (2006.01)
(Continued)

(52) U.S. Cl.
CPC .............. *A61B 1/24* (2013.01); *A61B 1/00066* (2013.01); *A61B 1/00121* (2013.01); *A61B 1/0684* (2013.01); *A61B 1/07* (2013.01); *A61B 1/32* (2013.01); *A61B 13/00* (2013.01)

(58) Field of Classification Search
CPC .............. A61B 1/06; A61B 1/24; A61B 13/00
USPC .................. 600/240, 241, 212, 213, 239, 237
See application file for complete search history.

(56) References Cited

U.S. PATENT DOCUMENTS 3,349,764 A  * 10/1967  Edinger ................... A61B 1/24
                                                        362/109
3,826,248 A  *  7/1974  Gobels .................... A61B 1/267
                                                        600/193
(Continued)

FOREIGN PATENT DOCUMENTS

| CN | 201091588 Y | 7/2008 |
| EP | 1433413 A2 | 6/2004 |
| WO | WO2007/124536 A1 | 11/2007 |

OTHER PUBLICATIONS

Acuneeds; Diagnostic Set (product info.); http://web.archive.org/web/20080722051852/http://www.acuneeds.com/products/equip.aspx?area=Treatment&cat=TDI&code=DIAG; printed Jul. 24, 2013.

(Continued)

*Primary Examiner* — Eduardo C Robert
*Assistant Examiner* — Julianna N Harvey
(74) *Attorney, Agent, or Firm* — Shay Glenn LLP

(57) ABSTRACT

A tongue depressor for illuminating an oral cavity, the tongue depressor including a handle which includes a light source and a switch for connecting a power supply to the light source. The tongue depressor also includes a blade for depressing the tongue, the blade being removably coupled to the handle, and wherein coupling the blade to the handle actuates the switch so that light emitted from the light source is transmitted by the blade into the oral cavity.

16 Claims, 10 Drawing Sheets

(51) Int. Cl.
*A61B 1/00* (2006.01)
*A61B 1/06* (2006.01)
*A61B 1/07* (2006.01)
*A61B 1/32* (2006.01)

(56) References Cited

U.S. PATENT DOCUMENTS

| | | |
|---|---|---|
| 3,916,881 A | 11/1975 | Heine |
| 4,643,172 A | 2/1987 | Taff et al. |
| 4,807,599 A | 2/1989 | Robinson et al. |
| 4,996,976 A | 3/1991 | Nakagawa |
| 5,318,009 A * | 6/1994 | Robinson ............... 600/241 |
| 5,656,014 A | 8/1997 | Rooney et al. |
| D422,081 S | 3/2000 | Wolf |
| 6,059,723 A | 5/2000 | Davis |
| 2007/0055112 A1* | 3/2007 | Lesko ............... A61B 1/00032 600/241 |
| 2008/0319290 A1* | 12/2008 | Mao ............... A61B 5/0086 600/323 |

OTHER PUBLICATIONS

Heine Optotechnik; Heine ClipLite Set with tongue depressor in hard case (product info.); http://web.archive.org/web/20070519105924/ http://www.aw-online.com/Shop/ShopProductDetail.asp?fdShopProductId=746; printed Jun. 13, 2013.

* cited by examiner

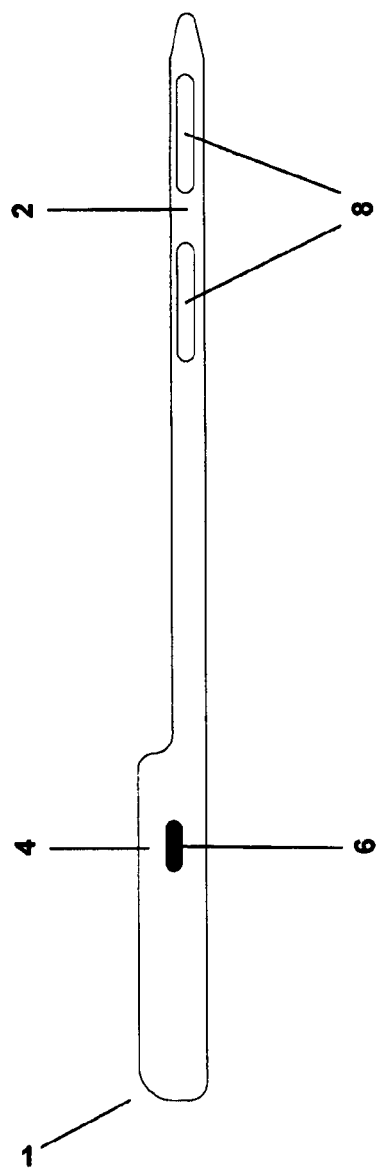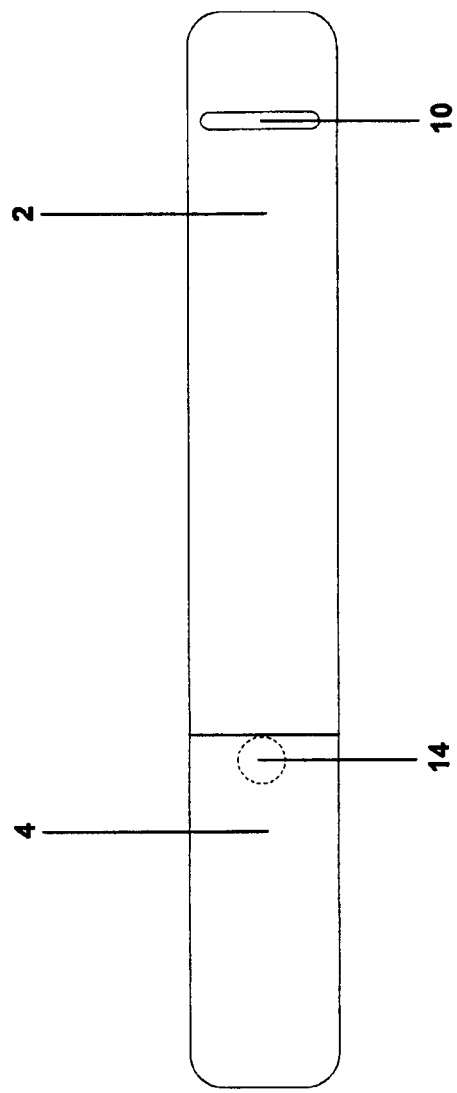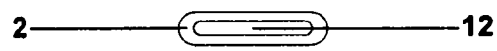
Figure 5A  Figure 5B
Figure 5C

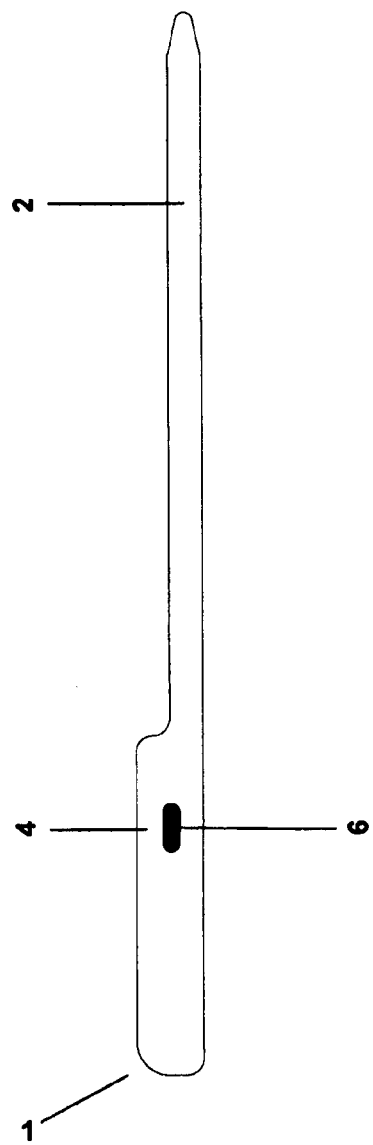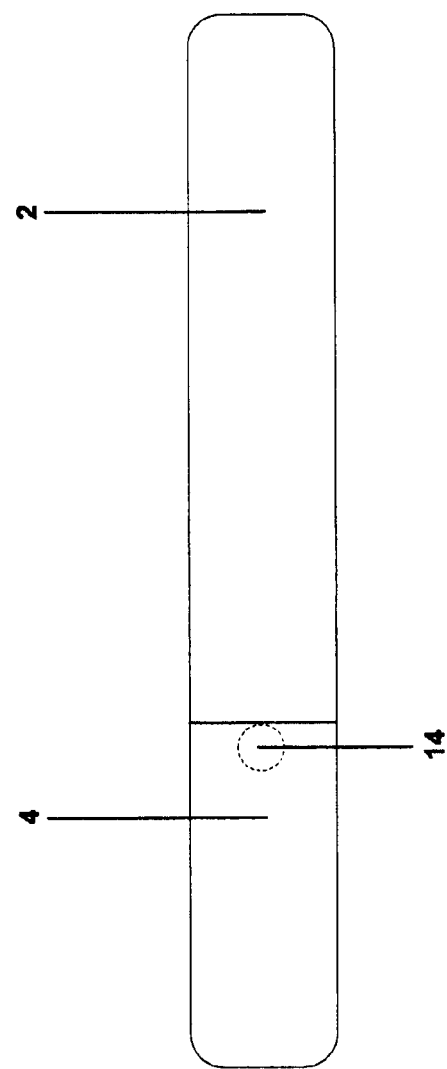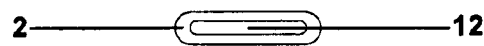
Figure 6A          Figure 6B
Figure 6C

TONGUE DEPRESSOR

FIELD OF THE INVENTION

The present invention relates to a tongue depressor for illuminating the oral cavity, and to methods of using the tongue depressor.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Medical personnel generally use a wooden spatula in one hand to depress the tongue of a subject when examining the oral cavity. To provide adequate illumination for the examination, the medical personnel must also direct light into the oral cavity, which generally involves the use of the other hand. The use of both hands can present difficulties for medical personnel as it may be advantageous to have a free hand for holding the subject's head in place when performing the examination, especially when the subject is a child.

U.S. Pat. No. 4,643,172 describes a luminescent tongue depressor having a luminiferous depressor element connected to a handle. An illuminating means, in the form of a monatomic gas contained within a vacuum tube, is positioned within the handle to illuminate the depressor element. Light dispersing grooves in the depressor element act to disperse the light transmitted from the illuminating means through the depressor element in the mouth. In use, a removable sheath may be used to protect the depressor element.

U.S. Pat. No. 5,656,014 describes an illuminated tongue depressor having an elongated unitary body with a depressor blade at one end and a battery at the other. The depressor blade is longitudinally curved, and has a lamp positioned on the blade so that in use the physician's hand is lowered relative to a patient's mouth. A sanitary sheath may be pulled over the depressor blade in use.

The use of a sheath in both U.S. Pat. Nos. 4,643,172 and 5,656,014 may be disadvantageous. For example, to remove the sheath from the depressor element or blade, an operator may need to handle a portion of the sheath which has been in contact with a patient's mouth. Furthermore, while the sheath may be sterile the depressor blade may require cleaning. This may make these tongue depressors less hygienic and more difficult to use.

To assist in examining a patient it may be advantageous to also generate light contrast within the oral cavity, which would make it easier for an operator to identify certain features within the oral cavity, such as swelling. It may be difficult to provide sufficient light contrast when using a wooden spatula and a torch, or with a lamp positioned towards the end of the depressor blade as in U.S. Pat. No. 5,656,014. Furthermore, the tongue depressor described in U.S. Pat. No. 4,643,172 is designed to be substantially omniluminescent and use of an omniluminescent depressor would provide even light within the oral cavity, generating minimal light contrast.

U.S. Pat. No. 4,807,599 discloses an illuminating tongue depressor which includes a handle and a depressor blade which may be decoupled from the handle. The blade is constructed of a light-conducting synthetic resin material of relatively thin cross-section. A light source is provided at the proximal end of the blade, and light is directed along the blade to the distal end. A relatively complex blade decoupling mechanism is provided in this tongue depressor, complicating manufacturing. Furthermore, the handle includes a large number of components which may also complicate manufacturing.

Accordingly, there is a need to provide a tongue depressor that is easy to use, relatively simple to manufacture and/or which in use provides a contrast in light within the oral cavity.

SUMMARY OF THE INVENTION

In a first broad form the present invention seeks to provide a tongue depressor for illuminating an oral cavity, the tongue depressor including:
  a) a handle which includes:
    i) a light source; and,
    ii) a switch for connecting a power supply to the light source; and,
  b) a blade for depressing the tongue, the blade being removably coupled to the handle, and wherein coupling the blade to the handle actuates the switch so that light emitted from the light source is transmitted by the blade into the oral cavity.

Typically the blade is a substantially solid body having a blade cavity at one end for receiving the handle.

Typically the blade includes a projection for engaging the switch when the handle and blade are coupled together.

Typically the projection is mounted in the blade cavity.

Typically the switch is positioned within a recess in the handle, such that the projection enters the recess when the handle and blade are coupled together.

Typically the handle includes at least two light sources.

Typically the at least two light sources are spaced apart in a direction parallel to a plane defined by the blade.

Typically the blade further includes at least one depression or projection adjacent the handle to assist an operator in decoupling the blade from the handle.

In a second broad form the present invention seeks to provide a tongue depressor for illuminating an oral cavity, the tongue depressor including:
  a) a handle which includes a plurality of light sources; and
  b) a blade for depressing the tongue, wherein light from the light sources is transmitted by the blade into the oral cavity.

Typically the blade is removably coupled to the handle so that when the blade is coupled to the handle light from the light sources is transmitted by the blade into the oral cavity.

Typically the at least two light sources are spaced apart in a direction parallel to a plane defined by the blade.

Typically the handle further includes a switch to connect a power supply to the light sources, and wherein coupling the blade to the handle actuates the switch, such that light is emitted from the light sources when the handle and blade are coupled together.

Typically the blade includes a projection for engaging the switch when the handle and blade are coupled together.

Typically the switch is positioned within a recess in the handle, such that the projection enters the recess when the handle and blade are coupled together.

Typically the blade further includes at least one depression or projection adjacent the handle, to assist an operator in decoupling the blade from the handle.

In a third broad form the present invention seeks to provide a tongue depressor for illuminating an oral cavity, the tongue depressor including:
  a) a handle which includes a light source; and b) a blade for depressing the tongue, the blade being removably coupled to the handle so that when the blade is coupled to the handle light from the light source is transmitted by the blade into the oral cavity, and wherein the blade includes at least one depression or projection adjacent the handle to assist an operator in decoupling the blade from the handle.

Typically the handle further includes a switch to connect a power supply to the light source, and wherein coupling the blade to the handle actuates the switch, such that light is emitted from the light source when the handle and blade are coupled together.

Typically the blade includes a projection for engaging the switch when the handle and blade are coupled together.

Typically the switch is positioned within a recess in the handle, such that the projection for actuating the switch enters the recess when the handle and blade are coupled together.

Typically the handle includes a plurality of light sources.

In a fourth broad form the present invention seeks to provide a tongue depressor for illuminating an oral cavity, the tongue depressor including:
 a) a handle which includes:
   i) a plurality of light sources; and,
   ii) a switch to connect a power supply to the light sources; and
 b) a blade for depressing the tongue, the blade being removably coupled to the handle, and wherein coupling the blade to the handle actuates the switch so that light emitted from the light sources is transmitted by the blade into the oral cavity, and wherein the blade includes at least one depression or projection adjacent the handle, to assist an operator in decoupling the blade from the handle.

Typically the blade includes a blade cavity for accommodating a portion of the handle when the handle and blade are coupled together.

Typically the blade is adapted to act as an optical waveguide for light emitted from the light source.

Typically the light source generates substantially no heat.

Typically the light source is a light-emitting diode.

Typically the handle further includes a power supply, wherein the power supply is a battery.

Typically the battery is a lithium-ion battery.

Typically the tongue depressor is for illuminating a selected region within the oral cavity.

Typically the blade is a solid body for emitting light substantially from at least one of a blade end and blade edges.

Typically the tongue depressor is for illuminating a selected region within the oral cavity, and wherein the blade includes one or more apertures for emitting light from the light source to illuminate a selected region within the oral cavity.

In a fifth broad form the present invention seeks to provide a tongue depressor for illuminating a selected region within the oral cavity, the tongue depressor including:
 a) a handle;
 b) a light source; and
 c) a blade attached to the handle for depressing the tongue, the blade including one or more apertures for emitting light from the light source to illuminate a selected region within the oral cavity.

Typically the blade includes an internal cavity with the apertures extending from the cavity to an outer surface of the blade, and wherein the light source is arranged for illuminating the internal cavity.

Typically the one or more apertures in the blade include one or more distal apertures for illuminating the oral orifice.

Typically the one or more apertures in the blade include one or more lateral apertures for illuminating one or both cheeks.

Typically the one or more apertures in the blade include two or more lateral apertures for illuminating both cheeks.

Typically the one or more apertures in the blade include one or more superior apertures for illuminating the palate.

Typically the blade includes one aperture. In one example, the aperture is a distal aperture. In another example, the aperture is a superior aperture for illuminating at least part of at least one of:
 a) the posterior oral cavity;
 b) part of the palate;
 c) part of the oral orifice; and,
 d) part of both cheeks.

Typically the tongue depressor is arranged so that substantially all light from the light source is emitted through the one or more apertures.

Typically the light source is located within the handle.

Typically the blade is removable.

Typically the tongue depressor is sealed for sterilisation.

Typically the tongue depressor further includes a rechargeable battery.

Typically each of the one or more apertures include a transparent window.

Typically the handle and/or the blade are made from one or more materials selected from: polystyrene, acrylonitrile butadiene styrene, polypropylene, polycarbonate and polymethylmethacrylate.

In a sixth broad form the present invention seeks to provide a blade for depressing the tongue, wherein the blade is configured to removably couple to a handle, the blade including at least one depression or projection positioned to assist an operator in decoupling the blade from the handle, and wherein the blade is adapted to act as an optical waveguide for light emitted from a light source in the handle.

In a seventh broad form the present invention seeks to provide a blade for depressing the tongue, wherein the blade is configured to removably couple to a handle, the blade including:
 a) a cavity for accommodating a portion of the handle; and
 b) a projection within the cavity for actuating a switch in the handle, wherein the blade is adapted to act as an optical waveguide for light emitted from a light source in the handle.

In an eighth broad form the present invention seeks to provide a handle of a tongue depressor, the handle including:
 a) a light source; and
 b) a switch to connect a power supply to the light source, wherein the handle is configured to removably couple to a blade for depressing the tongue, and wherein coupling the blade to the handle actuates the switch so that light emitted from the light source is transmitted by the blade into the oral cavity.

In a ninth broad form the present invention seeks to provide a handle of a tongue depressor, the handle including a plurality of light sources, wherein the handle is configured to removably couple to a blade for depressing the tongue, and wherein the light sources are positioned so that light emitted from the light sources is transmitted by the blade into the oral cavity.

In a tenth broad form the present invention seeks to provide a method of illuminating the oral cavity of a subject, including
 a) providing a tongue depressor including:
   i) a handle which includes:
     (1) a light source; and (2) a switch to connect a power supply to the light source; and ii) a blade for depressing the tongue, wherein the blade is removably coupled to the handle and wherein coupling the blade to the handle actuates the switch so that light emitted from the light source is transmitted by the blade into the oral cavity;

b) coupling the blade to the handle to actuate the switch; and c) depressing the tongue with the tongue depressor to illuminate the oral cavity.

In an eleventh broad form the present invention seeks to provide a method of illuminating the oral cavity of a subject, including a) depressing the tongue with a tongue depressor including:
   i) a handle which includes a plurality of light sources; and
   ii) a blade for depressing the tongue, wherein light emitted from the light sources is transmitted by the blade into the oral cavity; and,
b) illuminating the oral cavity.

In a twelfth broad form the present invention seeks to provide a method of illuminating the oral cavity of a subject, including a) depressing the tongue with a tongue depressor including:
   i) a handle which includes a light source; and
   ii) a blade for depressing the tongue, wherein the blade is removably coupled to the handle, and wherein the blade includes at least one depression or projection adjacent the handle, to assist an operator in decoupling the blade from the handle and wherein light emitted from the light source is transmitted by the blade into the oral cavity;
b) illuminating the oral cavity.

In a thirteenth broad form the present invention seeks to provide a method of illuminating the oral cavity of a subject, including a) providing a tongue depressor including:
   i) a handle which includes:
      (1) a plurality of light sources; and
      (2) a switch to connect a power supply to the light sources; and
   ii) a blade for depressing the tongue, wherein the blade is removably coupled to the handle, and wherein the blade includes at least one depression or projection adjacent the handle, to assist an operator in decoupling the blade from the handle and wherein coupling the blade to the handle actuates the switch so that light emitted from the light sources is transmitted by the blade into the oral cavity;
b) coupling the blade to the handle to actuate the switch; and
c) depressing the tongue with the tongue depressor to illuminate the oral cavity.

In a fourteenth broad form the present invention seeks to provide a method of illuminating the oral cavity of a subject, including a) depressing the tongue with a tongue depressor including:
   i) a handle;
   ii) a light source; and
   iii) a blade attached to the handle for depressing the tongue, the blade including one or more apertures for emitting light from the light source to illuminate a selected region within the oral cavity; and b) illuminating a selected region of the oral cavity.

BRIEF DESCRIPTION OF THE DRAWINGS

An example of the present invention will now be described with reference to the accompanying drawings, in which:

FIG. 5A is a side view of a second example tongue depressor;

FIG. 5B is a plan view of the example tongue depressor of FIG. 5A showing the position of a light source;

FIG. 5C is a front view of the example tongue depressor of FIG. 5A;

FIG. 6A is a side view of a third example tongue depressor;

FIG. 6B is a plan view of the example tongue depressor of FIG. 6A showing the position of a light source;

FIG. 6C is a front view of the example tongue depressor of FIG. 6A;

DETAILED DESCRIPTION OF THE PREFERRED EMBODIMENT

Example tongue depressors for illuminating an oral cavity will now be described with reference to FIGS. 1 to 8.

Figure 1A:
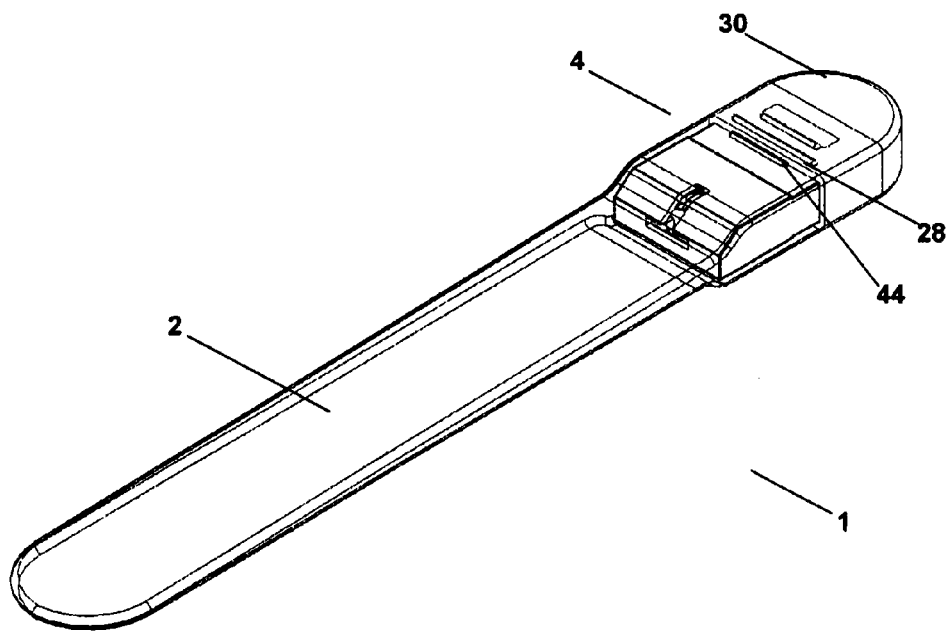
FIG. 1A is a perspective view of an example tongue depressor.
Figure 1B:
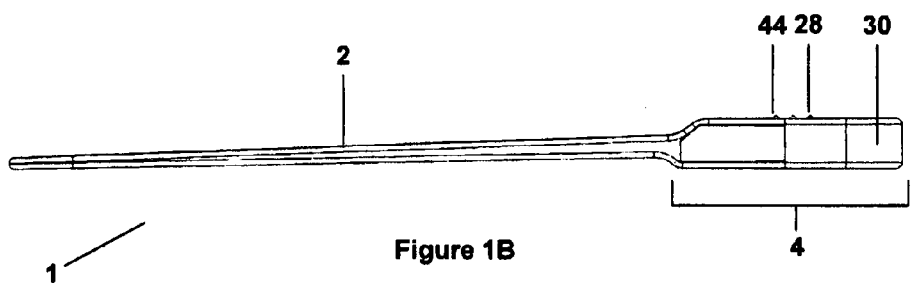
FIG. 1B is a side view of the example tongue depressor of FIG. 1A.
Figure 1C:
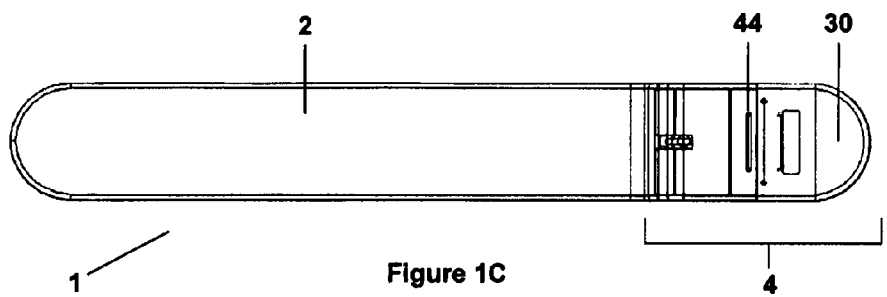
FIG. 1C is a plan view of the example tongue depressor of FIG. 1A.
Figure 2A:
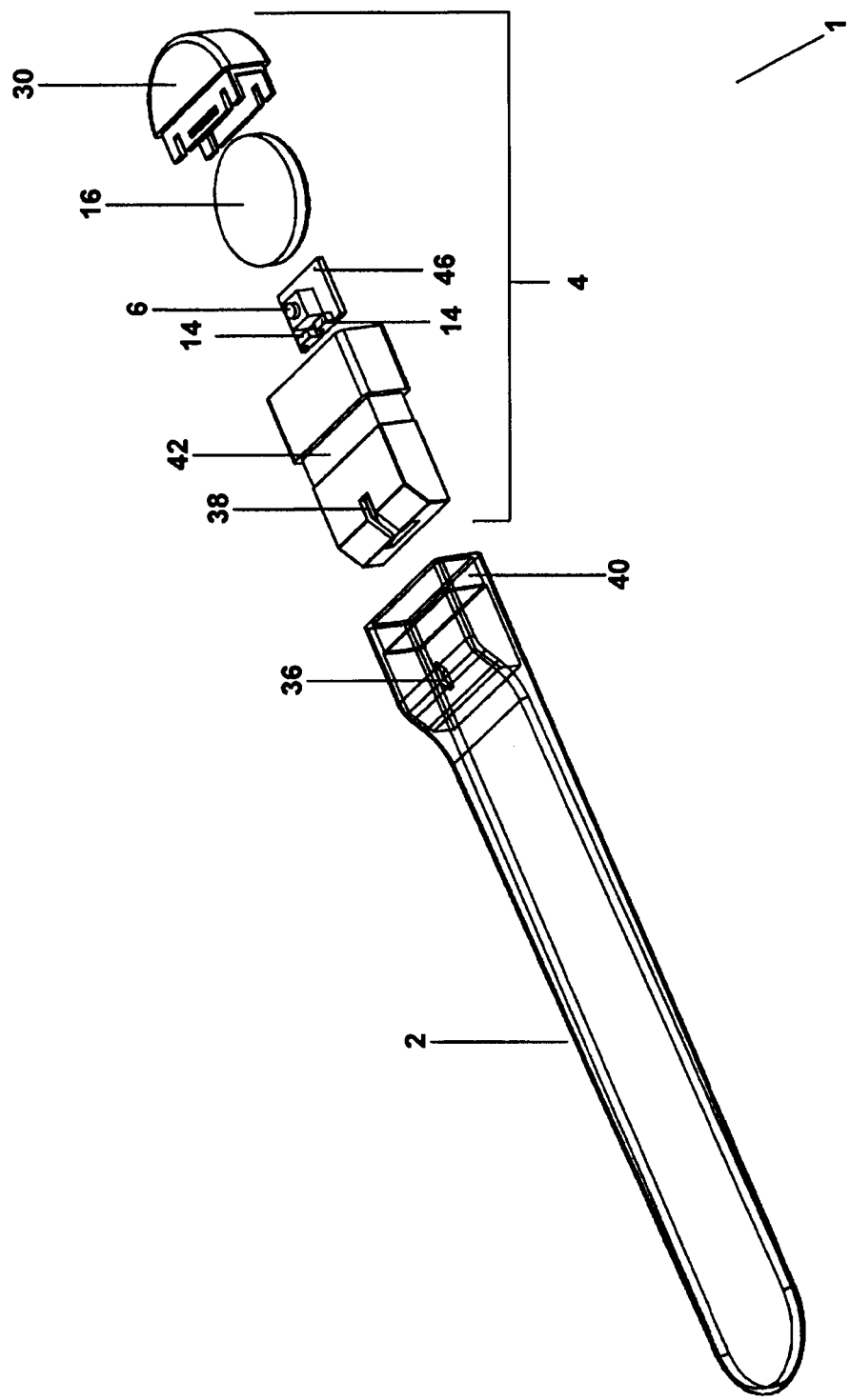
FIG. 2A is an exploded perspective view of the example tongue depressor of FIG. 1A illustrating the components.
Figures 2B, 2C:
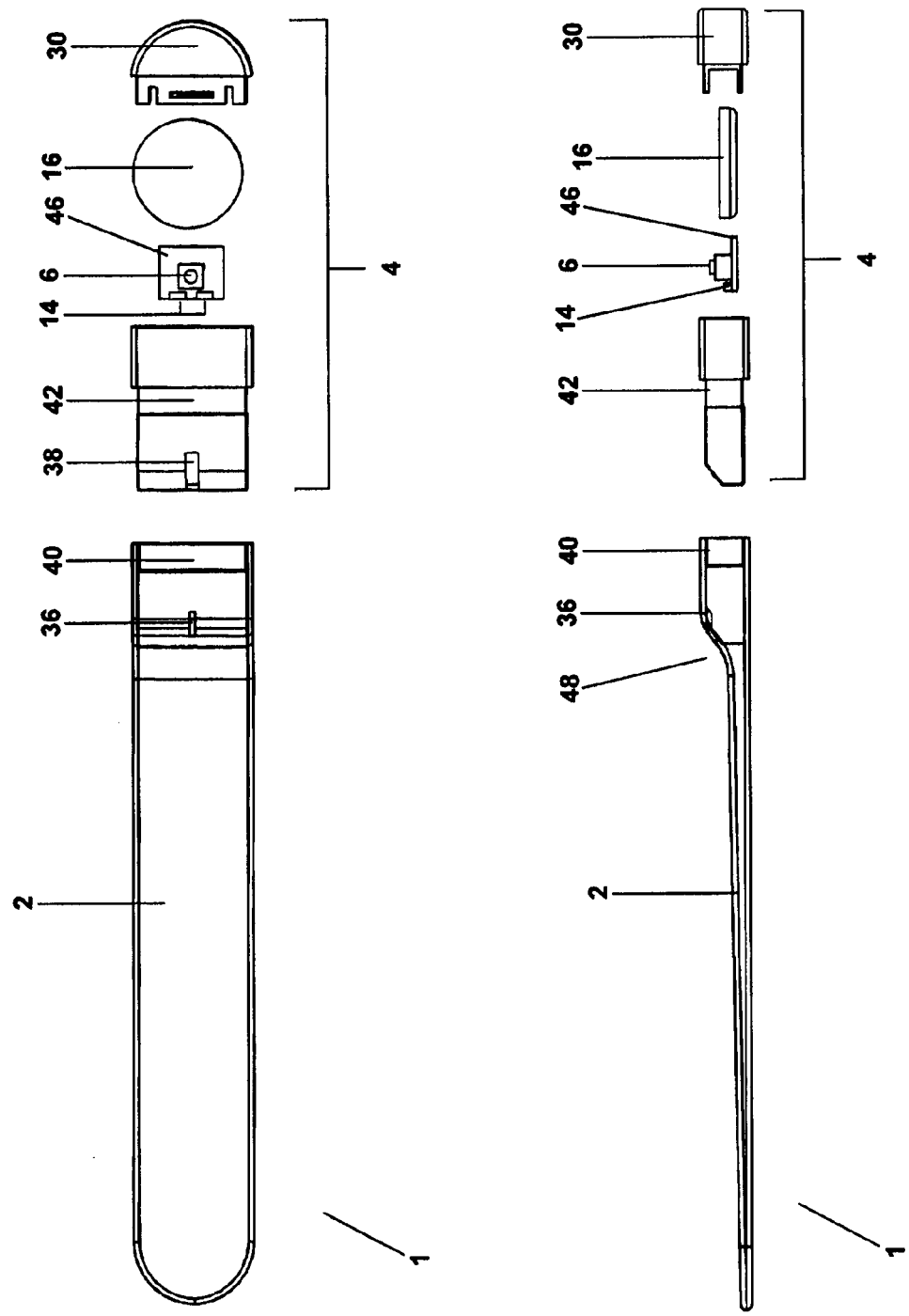
FIG. 2B is a plan view of the exploded example tongue depressor of FIG. 2A.
FIG. 2C is a side view of the exploded example tongue depressor of FIG. 2A.
Figure 3:
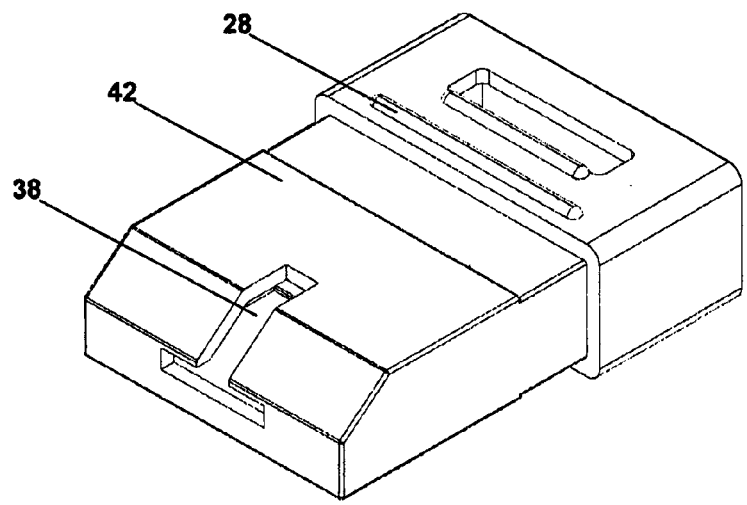
FIG. 3 is a perspective view of part of the handle of the tongue depressor of FIG. 1A.
Figure 4:
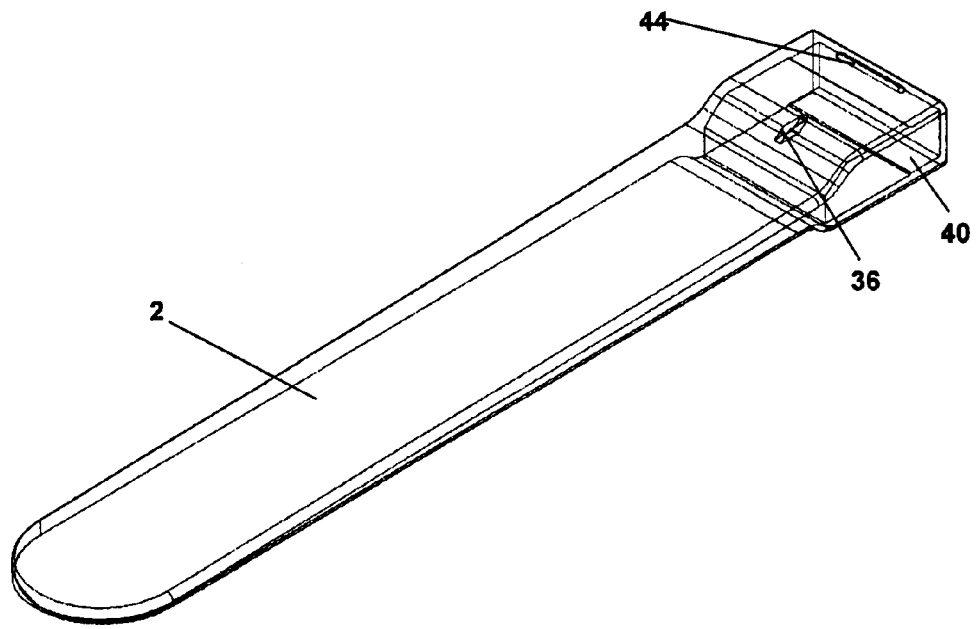
FIG. 4 is a perspective view of the blade of the tongue depressor of FIG. 1A.

FIGS. 1 and 2 illustrate a tongue depressor 1 which includes a blade 2, and a handle 4. The blade 2 is configured to removably couple to the handle 4. The handle includes a light source 14, and the tongue depressor 1 is configured so that light emitted from the light source 14 is transmitted by the blade 2 into the oral cavity, when the handle 4 and blade 2 are coupled together. FIG. 3 illustrates part of handle 4, and FIG. 4 illustrates blade 2.

When the tongue depressor is used by an operator, it may be held by handle 4, and the blade 2 may be used to depress the tongue. Light emitted from the light source 14 is transmitted through the blade 2 and illuminates the oral cavity. Accordingly, the term "blade", as used herein, relates to the portion of the tongue depressor which may be used to depress the tongue of a subject. In one example, the blade is substantially laminar. The surface of the blade for depressing the tongue of the subject may be, for example, curved or flat.

The blade 2 of the tongue depressor 1 illustrated in FIGS. 1 and 2 is detachable. Advantageously, the blade 2 may be disposable so that a new, sterile blade may be used for each use. Alternatively, the detached blade 2 may be sterilised to allow reuse. In either case, this tongue depressor 1 may be handled hygienically without requiring use of a protective sheath for the blade 2.

In one example, the handle includes a switch 6 to connect a power supply to the light source 14. The switch 6 may be multi-positionable, and may especially allow variable intensities of light to be emitted from the light source 14.

In the current example, coupling the blade 2 to handle 4 actuates the switch 6, such that light is emitted from the light source 14 when the handle 4 and blade 2 are coupled together. Advantageously, this arrangement permits simple operation by an operator, such as medical personnel or a member of the general public, by allowing the operator to activate the light source by simply coupling the handle 4 and blade 2 together, thereby avoiding the need to actuate a separate switch and allowing single handed operation.

To achieve this, as illustrated in FIGS. 1 and 2, the blade 2 may include a projection 36 for actuating the switch 6 when the handle 4 and blade 2 are coupled together. The switch 6 may also be positioned within a recess 38 in the handle 4, so that the projection 36 enters the recess 38 and engages the switch 6, when the handle 4 and blade 2 are coupled together.

In the current example, the blade 2 includes a cavity 40 for accommodating a portion of the handle 42 when the handle 4 and blade 2 are coupled together. In this example, the projection 36 is located within the cavity 40, and the recess 38 is located within the portion of the handle 42, so that when the handle 4 and blade 2 are coupled together, the projection 36 engages the switch 6 and activates the light source 14.

It will be appreciated that this arrangement allows the light source 14 to be automatically activated when the blade 2 and handle 4 are coupled together, thereby avoiding the need for an operator to depress an additional switch, which in turn makes the device easier use. Additionally, by having the switch 6 contained in a recess 38 this avoids a switch being inadvertently activated resulting for example in the battery being wasted when it is not intended to use the tongue depressor.

In another example (such as in the example of FIG. 8) the handle 4 may include a cavity for accommodating a portion of the blade 2 when the handle 4 and blade 2 are coupled together, in which case a similar corresponding arrangement may be used to activate the light source 14.

In a further example, the switch 6 may be located on the exterior of the handle (such as in the examples of FIGS. 5-8), so that the switch may be actuated by the operator after the handle and blade are coupled together.

The blade 2 may couple to the handle 4 by any suitable mechanism, such as a clip-fit, friction-fit, interference-fit or the like. The blade 2 is especially coupled to the handle 4 using one or more projections or depressions in the blade 2 which cooperate with corresponding depressions or projections in the handle 4.

In another example, the blade 2 and handle 4 may include at least one projection or depression to assist the operator in handling the tongue depressor 1, and in particular in decoupling the blade 2 from the handle 4. For example, the blade 2 and/or handle 4 may especially include a plurality of projections or depressions, more especially a plurality of projections, most especially a plurality of ridges 28 (including ridge 44).

Advantageously, the presence of at least one depression or projection adjacent the handle 4 (as at 44) allows the operator to hygienically detach the blade 2 from the handle 4 without touching the portion of the blade 2 that has come into contact with the patient's oral cavity. For example, the at least one depression or projection may be pushed or "flicked" by the operator to detach the blade 2. This arrangement also may be relatively simple to manufacture.

Advantageously, the tongue depressor 1 may be used for illuminating a selected region within the oral cavity of a patient. This allows an operator to alter the region illuminated by moving the tongue depressor 1 within the oral cavity. In this manner enhanced light contrast is provided, allowing the operator to more readily notice certain features within the oral cavity. For example, changes in shadows resulting from the emitted light would allow swelling to be more readily observed.

In one example a selected region within the oral cavity may be illuminated by configuring the tongue depressor 1 so that substantially all light emitted from the light source 14 is emitted from the blade 2 at the distal portion of the blade 2 to the handle 4 when the tongue depressor 1 is used. This arrangement allows the tongue depressor 1 to especially illuminate the rear of the oral cavity. However, in other examples some light may be emitted from the blade 2 closer to handle 4. In a further example, some light may be emitted from the blade 2 at the distal portion of the blade 2 to the handle 4, and some light may emitted from the blade 2 closer to handle 4, for example at 48 (see FIG. 2C).

In one example, emission of light from the distal portion of the blade 2 to the handle 4 is achieved by having the blade 2 act as an optical waveguide for light emitted from the light source 14. The blade 2 advantageously may be relatively thin, which provides a shallow angle of incidence for light impinging on an inner surface of the upper and lower faces of the blade 2. This ensures the light is internally reflected and undergoes a minimal number of internal reflections within the blade 2 so that light emitted from the light source 14, and especially substantially all light emitted from the light source 14, is emitted at a distal portion of the blade 2 relative to the handle 4. Additionally, with this arrangement light may also be emitted from edges of the blade 2, when the tongue depressor 1 is used, thereby providing further illumination within the oral cavity.

In some examples, the surface of the blade 2 may be configured to control the passage of light. For example, the surface of the blade 2 may be smooth. This improves internal reflection for light passing through the blade 2, resulting in most, if not substantially all light passing through to the distal end of the blade 2. Alternatively, the surface of the blade may be roughened. This improves scattering of light passing through the blade 2, resulting in the emission of less light from the distal end of the blade 2 and the emission of more light from other portions of the blade 2. The thickness of the blade 2 may also be used to control the passage of light, as the thinner the blade the more light is expected to pass through to the distal end of the blade 2.

To provide a waveguide for light emitted from the light source 14, the blade 2 is especially a solid body extending from adjacent the light source 14 (when the handle 4 and blade 2 are coupled together) to the distal end of the blade 2 (see FIGS. 1, 2 and 4). In this example, the light source 14 is positioned adjacent to an opening in the portion of the handle 42, so that visible radiation from the light source passes through the opening and into the solid body of the blade 2, thereby maximising transmission of light into the blade 2. Accordingly, in this instance, the blade 2 does not include an internal cavity, thereby making the blade 2 easier to manufacture.

In a further example, a portion of the surface of blade 2 may be adapted to reflect light into the blade 2. For example, this may include a surface coating which has one or more apertures to allow light to exit the blade 2.

In the example illustrated in FIGS. 1, 2 and 4 the blade is transparent and does not include any apertures for emitting light. In this instance, light is typically emitted from at least one of a blade end and blade edges, with only minimal amounts of light being emitted from the upper and lower faces of the blade 2.

In this example, the blade 2 may be made of any suitable materials which are capable of transmitting light. For example, the blade may be made of a plastic, especially poly(methyl methacrylate) or polycarbonate, especially polycarbonate. Advantageously, polycarbonate is recyclable, optically transparent and is not brittle. The blade is especially made from an injection moulded plastic.

In other examples, the blade 2 includes one or more apertures 8, 10, 12 (see FIGS. 5-8) for emitting light from the light source 14 to illuminate a selected region within the oral cavity. In this example, the blade 2 may include an internal cavity 18, with the apertures 8, 10, 12 extending from the cavity 18 to an outer surface of the blade 2. The light source 14 may be arranged to illuminate the cavity 18.

As used herein, the term "aperture" relates to a region through which light is emitted from the blade. The apertures may be a hole in the blade 2, or may include a transparent window. The aperture may include a transparent window that occupies a portion of the tip of the blade, for example as in 10 in FIG. 8.

In one example, the handle 4 of the tongue depressor 1 includes a plurality of light sources 14. The plurality of light sources 14 may be especially positioned so as to extend laterally across the handle 4, as illustrated in FIG. 2A. Thus, the light sources 14 are spaced apart in a direction parallel to a plane defined by the blade 2. Including a plurality of light sources spaced apart in this manner ensures light enters the blade 2 at a number of different locations, which can provide improved illumination and contrast when the tongue depressor 1 is used to illuminate the oral cavity of a subject. In particular, improved contrast may occur as a plurality of light sources 14 provides more light and increased shadows within the oral cavity when the tongue depressor 1 is used.

The example illustrated in FIGS. 1 and 2 shows two light sources 14, although the handle 4 may include 1, 2, 3, 4 or 5 light sources 14, especially 1, 2 or 3 light sources 14, more especially 1 or 2 light sources 14, most especially 2 light sources 14.

Any suitable light source 14 may be used in the tongue depressor 1. Exemplary light sources 14 include an incandescent bulb (including a halogen bulb), a fluorescent lamp, a high-intensity discharge lamp, a low-pressure sodium lamp, a light-emitting diode, a gas-discharge lamp and a monatomic gas bulb such as krypton or xenon. However, typically the light source or plurality of light sources 14 in the handle 4 are light-emitting diodes (LEDs), such as surface mount LEDs. LEDs typically use less energy than other forms of light source, thereby maximising battery life. Additionally, LEDs typically generate less heat than other forms of light source, thereby preventing the handle from overheating. Overheating may occur, for example, if incandescent or other light sources are used, and overheating may result in distortion of the handle 4 and/or the blade 2, or patient discomfort when the depressor is used.

The light source may be connected to a power supply through a switch 6, especially on a circuit board 46. The circuit board may include other components, such as resistors and the like, although in one example, the circuit board consists of a light source 14, a switch 6 and a connection for a power supply. The circuit may consist of, for example, two surface mounted LEDs in parallel, a switch in series and a battery.

A power supply may be present within the handle 4, such as a battery 16. Suitable batteries for use in the tongue depressor 1 include a battery selected from: zinc-carbon, zinc-chloride, lithium, alkaline, nickel-cadmium, nickel-metal hydride, lead-acid and lithium ion, although any suitable power supply could be used. The battery is especially a lithium-ion battery, more especially a CR2032 battery. The handle 4 may also include a removable cover 30 for allowing the battery 16 to be removed and replaced as required. The handle may also include a fastener for cover 30, such as a screw to secure the cover 30 closed. The use of such a fastener may be advantageous for child safety, for example.

In one example, the battery 16 is located within the portion of the handle 4 opposite to the blade 2, however this is not essential and any suitable position could be used. The battery may be replaceable and/or rechargeable. For example, the battery may be charged by coupling the tongue depressor to a power cord. In another example, the battery may be charged by inductive charging. In some examples, the battery in the tongue depressor is not replaceable. For example, the handle may not include removable cover 30 to access the battery 16, so that the handle 4 is replaced when the battery 16 is depleted. In this example, the outer shell of handle 4 may be formed from a single piece of plastic, especially a single piece of injection moulded plastic.

In another example, the tongue depressor does not include a battery. For example, the light source 14 in the tongue depressor may be powered by electricity from an external power supply when in use.

The handle may be made of a material such as a moulded plastic, especially a thermosetting plastic or a thermoplastic. The handle especially may be made from a material selected from: polystyrene, acrylonitrile butadiene styrene (ABS), polypropylene, polycarbonate and polymethylmethacrylate, especially acrylonitrile butadiene styrene (ABS). The handle is especially made using an injection moulded plastic.

The handle 4 and blade 2 may be manufactured and/or sold separately. In either case, the blade may be sold in a sterile form, for example provided sterilised in packaging, allowing the blade to be used as a single use disposable item. The blade may alternatively be sterilisable for repeated use.

In a further example, the blade 2 is integrally formed with handle 4. In this example, the blade 2 is not removably coupled to the handle 4, and the outer shell of blade 2 and handle 4 may be formed from a single piece of plastic, especially a single piece of injection moulded plastic. In this example, the tongue depressor 1 may be sterilisable for repeated use, or may be sold in a sterile form, for example provided sterilised in packaging, allowing the tongue depressor 1 to be used as a single use disposable item.

In some examples, the handle 4 includes a keyring attachment, allowing the handle 4 to be easily carried by an operator. The handle can then easily be attached to a blade 2 when tongue depressor 1 is to be used.

FIG. 5 illustrates an second example tongue depressor, for illuminating a selected region within the oral cavity, the tongue depressor including a handle 4, a light source 14 and a blade 2 attached to the handle for depressing the tongue, the blade including apertures 8, 10 and 12 for emitting light from the light source 14 to illuminate a selected region within the oral cavity.

Advantageously, the apertures 8, 10 and 12 in the blade 2 allow directed illumination to be provided to a selected region within the oral cavity when the tongue depressor 1 is used. As discussed above, illuminating only a portion of the oral cavity provides an increased contrast in light, allowing the operator to more readily notice certain features, such as swelling, within the oral cavity.

The blade 2 may include distal apertures which can be used to illuminate the oral orifice. The tongue depressor illustrated in FIG. 5C shows one distal aperture 12, but it would be appreciated that any number of distal apertures may be present.

The blade 2 may also include one or more lateral apertures which can be used to illuminate one or both cheeks. The tongue depressor illustrated in FIG. 5A shows two lateral apertures 8, but it would be appreciated that any number of lateral apertures may be present. In the tongue depressor illustrated in FIG. 5 there are especially four lateral apertures for illuminating both cheeks, two on each side of the tongue depressor.

The blade 2 may also include one or more superior apertures which can be used to illuminate the palate. The tongue depressor illustrated in FIG. 5B has one superior aperture 10, but it would be appreciated that any number of superior apertures may be present.

The example illustrated in FIG. 5B includes a light source 14 located within the handle. In another example, the light source 14 may be located within the blade 2. Locating the light source 14 in the blade 2 may be advantageous, as this would decrease the distance that light would need to travel before it is emitted from the one or more apertures. This may provide more intense light. Any suitable light source 14 may be used, and exemplary light sources are as discussed above.

In one example, the tongue depressor 1 is arranged so that substantially all light from the light source 14 is emitted through the one or more apertures. In another example, some light from the light source 14 may be emitted through the blade 2 without passing through the one or more apertures. However, in this example less light may pass through the blade 2 than through the one or more apertures so that when the tongue depressor 1 is used, selected regions within the oral cavity are illuminated to a greater degree.

The blade 2 may be arranged so that light from the light source is emitted through the one or more apertures. For example, the blade 2 may include a transmission path extending from the light source 14 to the one or more apertures. This may be in the form of an internal cavity within the blade with the apertures extending from the cavity to an outer surface of the blade. In another example, the blade may include fibre optics which connect the light source 14 to the one or more apertures. In a further example, a separate light source 14 may be associated with each of the one or more apertures in the blade 2, so that the blade 2 may include one or more light sources 14. In another example, the blade 2 may be adapted to act as an optical waveguide for light emitted from the light source 14, such that no internal cavity is present.

The light source in the tongue depressor may be connected to a power supply, and the tongue depressor may also include a multi-positionable switch 6 to open or close the circuit between the power supply and the light source 14. In one example, the switch is located on the handle. The example illustrated in FIG. 5A includes a switch 6.

In the example illustrated in FIG. 5A, a power supply may be present within the tongue depressor 1, such as a battery 16. Suitable batteries for use in this tongue depressor 1 are as discussed above. In one example, the battery 16 is located within the portion of the handle 4 opposite to the blade 2 however this is not essential and any suitable position could be used. The battery 16 may be replaceable and/or rechargeable. For example, the battery 16 may be charged by coupling the tongue depressor to a power cord for charging. In another example, the battery may be charged by inductive charging. In some examples, the battery in this tongue depressor 1 is not replaceable. If this tongue depressor is to be sterilisable, then the charging method for the battery would need to be compatible with the sterilisation method. For example, it may be advantageous to employ inductive charging if the tongue depressor 1 is sealed for sterilisation.

In another example, the tongue depressor 1 does not include a battery. For example, the light source 14 in the tongue depressor 1 may be powered by electricity from an external power supply when in use.

Another example of a tongue depressor is illustrated in FIG. 6. This tongue depressor includes a blade 2, handle 4, switch 6 and light source 14 as in the example illustrated in FIG. 5. In this example there is only one aperture in the blade, distal aperture 12. This example tongue depressor may be used to illuminate the oral orifice, and this may be especially advantageous as the presence of only one aperture may provide increased light contrast during an examination.

Figure 7A:
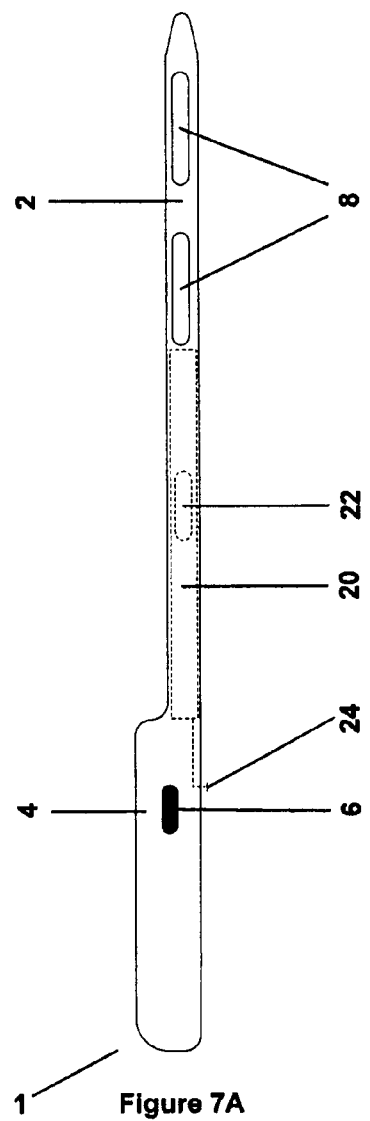
FIG. 7A is a side view of a fourth example tongue depressor.
Figure 7B:
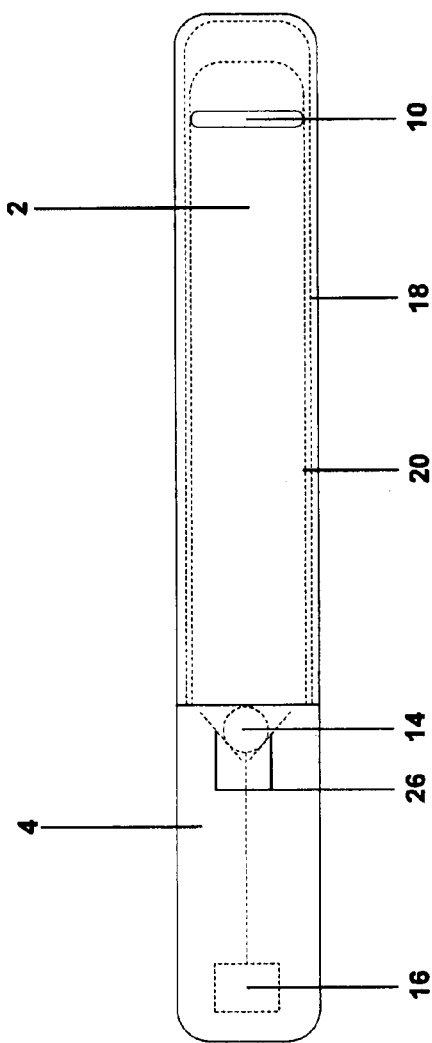
FIG. 7B is a plan view of the example tongue depressor of FIG. 7A showing the position of a light source.
Figure 7C:
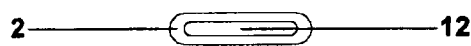
FIG. 7C is a front view of the example tongue depressor of FIG. 7A.

A further example of a tongue depressor is illustrated in FIG. 7. This tongue depressor includes a blade 2, handle 4, switch 6, light source 14 and apertures 8, 10, and 12 as in the example illustrated in FIG. 5. The tongue depressor of FIG. 7 also includes a battery 16 located within the portion of the handle opposite to the blade. An electrical circuit, which includes switch 6, connects battery 16 with light source 14. In one example, the electrical circuit is adapted to allow the light source to emit light at two or more defined intensities, for example using a multiple position switch, thereby allowing light at various intensities to be emitted from the apertures of the tongue depressor.

The example tongue depressor illustrated in FIG. 7 also includes an internal cavity 18 (see FIG. 7B), with the apertures extending from the cavity to an outer surface of the blade. The light source is arranged to illuminate the cavity.

In this example, the intensity of the light emitted from the apertures would be dependent on the ability of the internal cavity to transmit light to the apertures. Consequently, in one example the internal cavity 18 includes a reflective coating.

The tongue depressor may also include one or more reflectors to reflect the light from the light source towards the one or more apertures. This would promote reflection of the light within the internal cavity, thereby increasing the intensity of the light emitted from the one or more apertures or allowing light to be emitted more equally through each of the one or more apertures. The example illustrated in FIG. 7B includes two reflectors 26, which are positioned so that the light source 14 is located between the reflectors 26 and the internal cavity 18.

The example illustrated in FIGS. 7A and 7B also includes a movable sheath 20 for blocking the light transmitted through apertures 8, 10 and 12, or for altering the amount of light transmitted through these apertures. If the sheath is used to alter the amount of light transmitted through the one or more apertures, it may include an aperture of a smaller size. As illustrated in FIG. 7A, aperture 22 may reduce the amount of light emitted through a lateral aperture 8 if the sheath is moved into the appropriate position. In the example illustrated in FIG. 7, the sheath is movable via handle 24, but other methods of moving the sheath may also be used.

In a further example, the blade 2 of the tongue depressors 1 illustrated in FIGS. 5-8 are removable from the handle 4 so that a new blade may be used with each subject. In this example, the handle 4 may include one or more holding members to hold the blade in place when it is attached. The handle 4 may also include one or more releasing members to release the blade from the handle. In one example, the handle 4 is arranged so that the blade 2 is released without requiring direct contact between an operator and the blade 2. In these examples, the blade 2 may be disposable. The blade 2 may be coupled to the handle 4 using a clip-fit, friction-fit, interference-fit or the like. If the blade 2 is removable then the light source 14 is especially located within the handle 4. In this case, the blade 2 may include an internal cavity 18 for illumination by the light source 14, fibre optics to connect the light source 14 and the one or more apertures, or the blade 2 may include no internal cavity.

In another example, the blade of the tongue depressor may include an aperture that includes a transparent window occupying a portion of the blade, especially the tip of the blade. This aperture can be used to illuminate all, or part of the posterior oral cavity, such as the palate, oral orifice and/or both cheeks, and in particular the posterior palate, oral orifice and both cheeks posteriorly. In one example this aperture is situated on a superior surface of the tongue depressor, extending from the distal and lateral sides part way along the superior surface of the blade. The aperture can extend up to 50 mm from the distal end, especially from 10 mm to 35 mm from the distal end, more especially from 15 mm to 30 mm from the distal end, more especially from 20 mm to 25 mm from the distal end. An example of such a tongue depressor is illustrated in FIG. 8. This tongue depressor 1 includes blade 2, handle 4, switch 6, aperture 10 and light source 14 as in the example illustrated in FIG. 5. The aperture 10 in FIG. 8 is a single superior aperture that occupies a portion of the tip of the blade 2 which can be used to illuminate the palate, oral orifice and/or both cheeks.

Figure 8A:
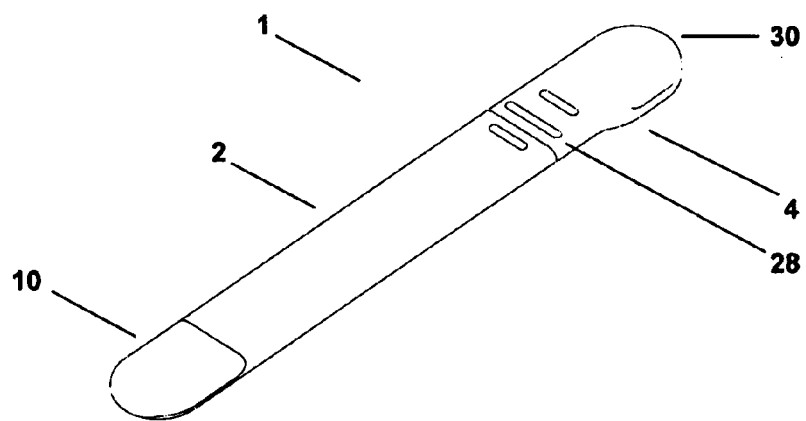
FIG. 8A is a perspective view of a fifth example tongue depressor.
Figure 8B:
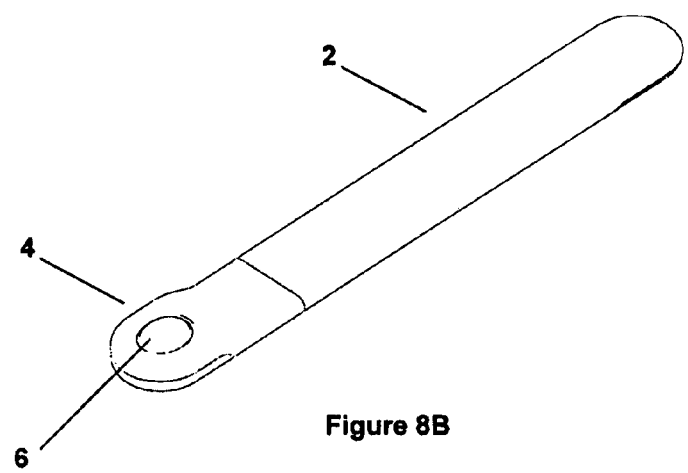
FIG. 8B is a perspective view of the example tongue depressor of FIG. 8A.
Figure 8C:
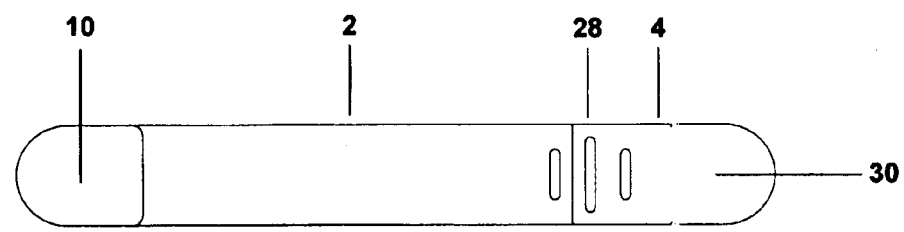
FIG. 8C is a plan view of the example tongue depressor of FIG. 8A.
Figure 8D:
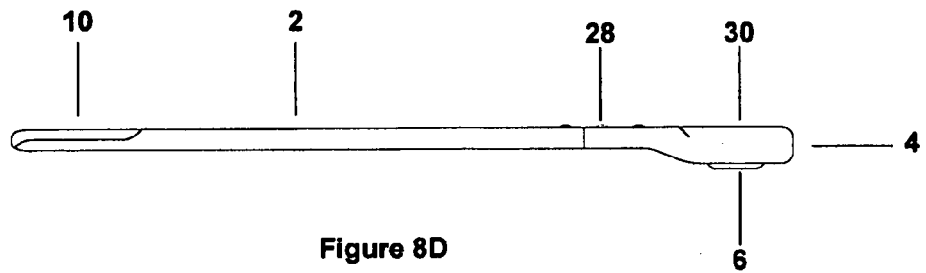
FIG. 8D is a side view of the example tongue depressor of FIG. 8A.
Figure 8E:
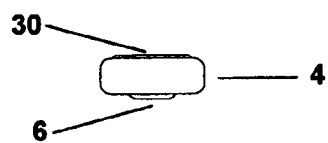
FIG. 8E is a rear view of the example tongue depressor of FIG. 8A.
Figure 8F:
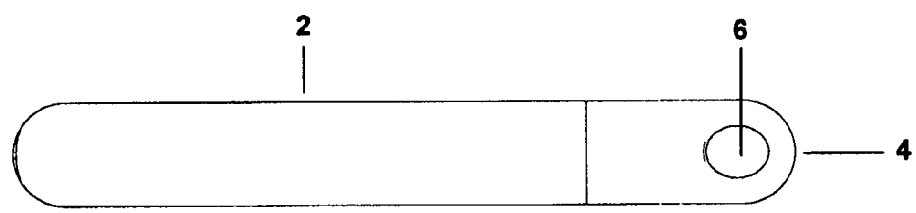
FIG. 8F is a plan view of the example tongue depressor of FIG. 8A.
Figure 8G:
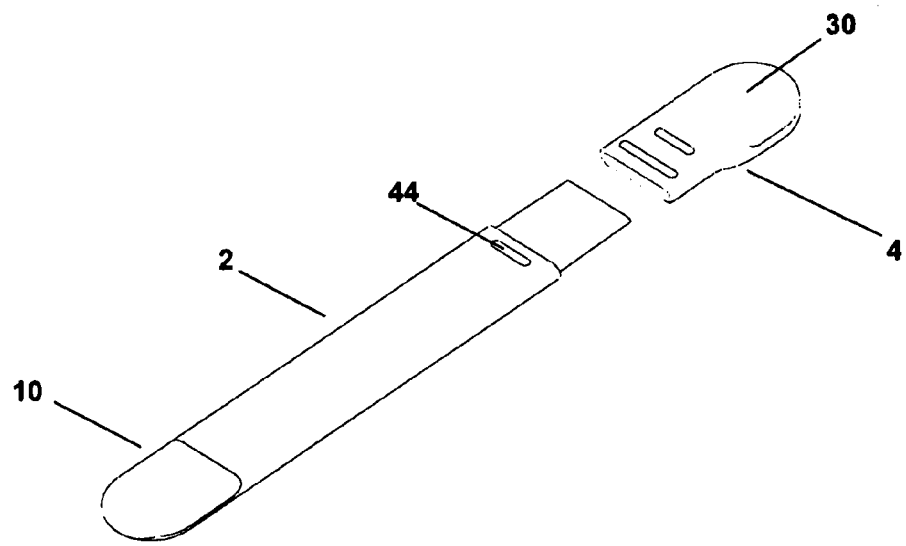
FIG. 8G is a perspective view of the example tongue depressor of FIG. 8A showing a removable blade.
Figure 8H:
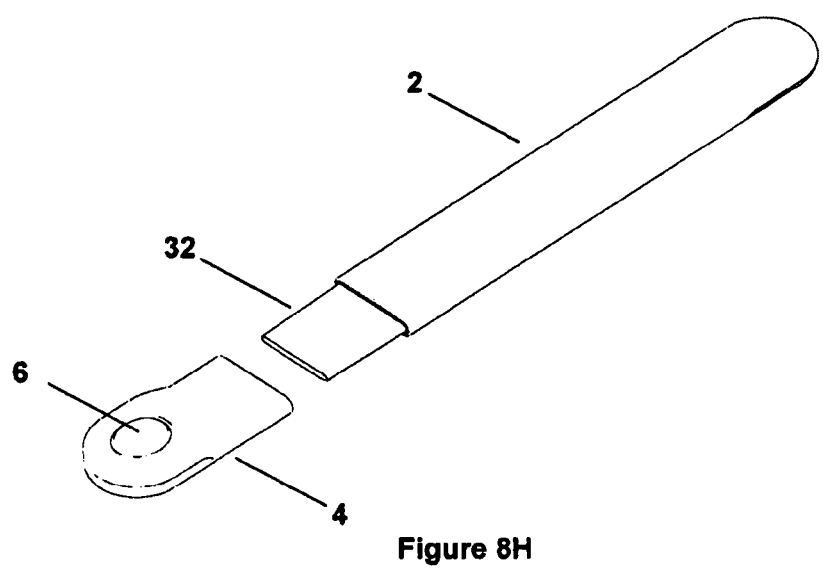
FIG. 8H is a perspective view of the example tongue depressor of FIG. 8A showing a removable blade.
Figure 8I:
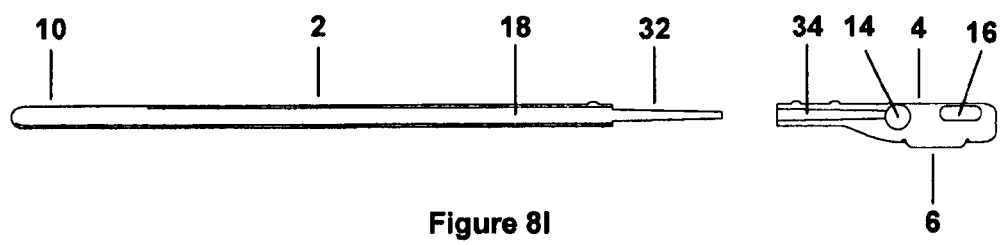
FIG. 8I is a cross-sectional view of the example tongue depressor of FIG. 8A showing a removable blade.

The blade 2 of the tongue depressor 1 is removable from the handle in the example illustrated in FIG. 8 (see FIG. 8G to 8I). In this example the blade includes member 32 that may be fitted into cavity 34. When the blade is fitted to the handle, member 32 defines part of the internal cavity 18 (see FIGS. 8H and 8I). While the tongue depressor illustrated in FIG. 8 shows the aperture 10 and switch 6 located on opposite sides of the tongue depressor, it would be appreciated that the blade can be fitted to the handle such that the aperture and switch are located on the same side.

When the blade and the handle are fitted together, a light source 14 is positioned to illuminate the internal cavity 18, and as illustrated in FIG. 8I aperture 10 extends from the cavity to the surface of the blade. In the example illustrated in FIG. 8I the light source 14 is located within the handle 4, and switch 6 is located on the handle 4. A battery 16 is also located within handle 4, and an electrical circuit, which includes switch 6, would connect battery 16 with light source 14. The handle also includes a cover 30 to access the battery (as illustrated in FIGS. 8A, 8C to 8E and 8G).

The surface of the tongue depressor may also be adapted to allow the operator's fingers and thumb to more easily hold the tongue depressor. For example, the handle and/or blade of the tongue depressor may include one or more depressions for the fingers and/or thumb. The tongue depressor may also include one or more projections, especially ridges, in the handle and/or blade for the fingers and/or thumb. The example illustrated in FIG. 8 includes a series of ridges 28 for the thumb of the operator on the handle and blade. One of these ridges (44) may be used to assist the operator to decouple the blade and handle.

Before the tongue depressor is used to examine different subjects, at least the portion to be inserted into the oral cavity of the subject may need to be sterile. For example, if the blade is removable then the removable blade may be provided in a sterile form. For example, blade 2 in the example illustrated in FIG. 8 may be disposable. In a further example, a disposable sleeve may be used to cover the portion of the blade of the tongue depressor to be inserted into the oral cavity of the subject. In these examples, the non-disposable portions of the tongue depressor should not require sterilisation.

All, or part of the tongue depressor may require sterilisation, especially if the blade is fixed to the handle. In one example, a portion of the blade is sterilisable. In another example, the entire tongue depressor is sterilisable. In a further example only the blade is sterilisable. A tongue depressor which is partially, or entirely, sterilisable may be advantageous as it would not require the disposal of, for example, replaceable blades for recycling or landfill.

If sterilisation of all or part of the tongue depressor is intended, the materials used to construct the tongue depressor must be appropriate. This is especially important if the entire tongue depressor is sterilisable. For example, if all or part of the tongue depressor is to be sterilised by a chemical method, then substantially none of the chemical sterilisation agent should enter the electrics in the blade or handle during sterilisation. In this example if the blade includes apertures, these may include a window of a material that is substantially light transmissive and which will not become opaque after repeated sterilisation.

In another example, if all or part of the tongue depressor is to be sterilised using a heated liquid, then substantially none of heated liquid should enter the electrics in the blade or handle. In this example if the blade includes apertures, these may include a window of a material that is substantially light transmissive. In this case if the power supply and the light source are present in the blade or handle to be sterilised, the power supply and the light source must also be selected so that these components will continue to function after repeated heating.

The blade and/or the handle in the examples of FIGS. 5-8 may be made of a material such as a moulded plastic, especially a thermosetting plastic or a thermoplastic. The blade and/or the handle may be made from a material selected from: polystyrene, acrylonitrile butadiene styrene (ABS), polypropylene, polycarbonate and polymethylmethacrylate.

Further materials may also be used to construct the blade and/or the handle of the examples of FIGS. 5-8. For example, if the blade is removable and includes an internal cavity, then the blade may be made from biodegradable materials, especially cellulosic materials such as wood fibres or cardboard. In this case, the aperture(s) may simply be holes in the blade to emit light.

The shape of the handle 4 and the blade 2 in FIGS. 1-8 are provided for the purpose of example only; any other suitable shape may be used. For example, blade 2 may be the same height as the handle 4 along all, or a substantial portion of, the length of the blade 2.

In one example, the length of the tongue depressor 1 (which includes the combined length of the blade 2 and the handle 4) is from 70 mm to 270 mm, especially from 90 mm to 250 mm, or from 110 to 230 mm, more especially from 130 to 210 mm, or from 150 mm to 190 mm, most especially about 170 mm.

The length of blade 2 alone may be, for example, from 50 to 250 mm, especially from 70 mm to 230 mm, or from 90 to 210 mm, more especially from 110 to 190 mm, or from 130 mm to 170 mm, most especially about 150 mm. The length of handle 4 alone may be, for example, 15 to 65 mm, especially from 20 mm to 60 mm, or from 25 to 55 mm, more especially from 30 to 50 mm, or from 35 mm to 45 mm, most especially about 40 mm. When present, the length of the portion of the handle 42 may be, for example, from 5 to 35 mm, especially from 10 to 30 mm, more especially from 15 mm to 25 mm, most especially about 20 mm.

In another example, the width of the tongue depressor 1 (including the blade 2 and/or the handle 4) is from 5 mm to 40 mm, more especially from 7 mm to 35 mm, more especially from 10 mm to 30 mm, more especially from 15 mm to 25 mm, most especially about 20 mm.

In a further example, the height of the blade 2 is from 0.5 mm to 10 mm, especially from 0.75 mm to 7.5 mm, more especially from 1 mm to 5 mm, more especially from 2 to 4 mm, more especially about 3 mm. In another example, the height of the handle 4 is from 0.5 mm to 70 mm, especially from 3 mm to 35 mm, more especially from 5 mm to 20 mm, more especially from 6 mm to 12 mm, more especially about 9 mm.

The above described examples demonstrate a number of different features, including for example, the activation of the light sources when the handle is coupled to the blade. It will be appreciated that the features of different examples can be used interchangeably and in conjunction, and that their description in separate examples is for the purpose of illustration only.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A tongue depressor for illuminating an oral cavity, the tongue depressor including:
    a) a handle having a handle body, wherein the handle includes:
       i) a light source entirely within the handle body; and,
       ii) a blade-coupling portion including a switch for connecting a power supply to the light source; and,
    b) a blade for depressing the tongue, the blade being removably coupled to the handle and including:
       (i) a blade cavity at one end for receiving the blade-coupling portion of the handle, and
       (ii) a solid body extending from the blade cavity to the end distal the blade cavity, wherein the solid body is configured to act as an optical waveguide for light emitted from the light source;
    wherein coupling the blade to the handle actuates the switch so that light emitted from the light source is transmitted by the blade into the oral cavity.

2. The tongue depressor according to claim 1, wherein the blade includes a projection mounted in the blade cavity for engaging the switch when the handle and blade are coupled together, and wherein the switch is positioned within a recess in the handle, such that the projection enters the recess when the handle and blade are coupled together.

3. The tongue depressor according to claim 1, wherein the handle includes at least two light sources.

4. The tongue depressor according to claim 3, wherein the at least two light sources are positioned so as to extend laterally across the handle.

5. The tongue depressor according to claim 1, wherein the blade further includes at least one depression or projection adjacent the handle to assist an operator in decoupling the blade from the handle.

6. The tongue depressor according to claim 1, wherein the light source is a plurality of light sources, and wherein the blade includes at least one depression or projection adjacent the handle to assist an operator in decoupling the blade from the handle.

7. The tongue depressor according to claim 1, wherein the light source generates substantially no heat.

8. The tongue depressor according to claim 7, wherein the light source is a light-emitting diode.

9. The tongue depressor according to claim 1, wherein the handle further includes a power supply, wherein the power supply is a battery.

10. The tongue depressor according to claim 9, wherein the battery is a lithium-ion battery.

11. The tongue depressor according to claim 1, wherein the tongue depressor is for illuminating a selected region within the oral cavity.

12. The tongue depressor according to claim 11, wherein the blade is a solid body for emitting light substantially from at least one of a blade end and blade edges.

13. The tongue depressor according to claim 1, wherein the tongue depressor is for illuminating a selected region within the oral cavity, and wherein the blade includes one or more apertures for emitting light from the light source to illuminate a selected region within the oral cavity.

14. The tongue depressor according to claim 1, wherein the blade cavity covers the blade-coupling portion of the handle when the handle and the blade are coupled together.

15. The tongue depressor according to claim 1, wherein the blade is transparent.

16. The tongue depressor according to claim 1, wherein the light source is located in the blade-coupling portion of the handle.

* * * * *